(12) United States Patent
Xin et al.

(10) Patent No.: US 8,956,634 B2
(45) Date of Patent: Feb. 17, 2015

(54) INSECT REPELLANT FABRICS HAVING NANOCAPSULES WITH INSECTICIDE

(75) Inventors: John Haozhong Xin, Kowloon (HK); Fei Bin, Kowloon (HK)

(73) Assignee: The Hong Kong Polytechnic University, Hung Hom (HK)

( * ) Notice: Subject to any disclaimer, the term of this patent is extended or adjusted under 35 U.S.C. 154(b) by 1174 days.

(21) Appl. No.: 11/822,047

(22) Filed: Jul. 2, 2007

(65) Prior Publication Data

US 2009/0010977 A1 Jan. 8, 2009

(51) Int. Cl.
- *A01P 17/00* (2006.01)
- *A01N 65/00* (2009.01)
- *A01N 25/34* (2006.01)
- *D06M 16/00* (2006.01)
- *A01N 53/00* (2006.01)
- *D06M 23/12* (2006.01)

(52) U.S. Cl.
CPC .............. *D06M 16/00* (2013.01); *A01N 53/00* (2013.01); *D06M 23/12* (2013.01)
USPC ............................................ 424/402; 514/65

(58) Field of Classification Search
USPC ......................................................... 424/402
See application file for complete search history.

(56) References Cited

U.S. PATENT DOCUMENTS

| | | | | |
|---|---|---|---|---|
| 4,765,982 A | * | 8/1988 | Ronning et al. | 424/403 |
| 5,238,682 A | * | 8/1993 | Akasaka et al. | 424/409 |
| 5,252,387 A | * | 10/1993 | Samson et al. | 442/67 |
| 5,503,918 A | | 4/1996 | Samson et al. | |
| 5,631,072 A | | 5/1997 | Samson et al. | |
| 5,759,569 A | * | 6/1998 | Hird et al. | 424/443 |
| 6,117,819 A | * | 9/2000 | Priesnitz et al. | 504/206 |
| 6,521,288 B2 | * | 2/2003 | Laks et al. | 427/180 |
| 6,582,714 B1 | | 6/2003 | Emmrich et al. | |

* cited by examiner

*Primary Examiner* — Johann R Richter
*Assistant Examiner* — Andrea Buckley
(74) *Attorney, Agent, or Firm* — Leydig, Voit & Mayer, Ltd.

(57) ABSTRACT

The present invention relates to method of manufacturing a prytheroid-treated fabric and manufactured products created thereby. Through the development and application of prytheroid nanocapsules to a fabric, the fabric exhibits insecticidal properties, even following successive washings and solar exposure.

21 Claims, 2 Drawing Sheets

INSECT REPELLANT FABRICS HAVING NANOCAPSULES WITH INSECTICIDE

BACKGROUND

Pyrethroids, including both the naturally occurring compounds and their synthetically prepared analogs effectively control a variety of pests, such as ticks, mites, cockroaches, houseflies, mosquitoes, black flies, fleas, and other flying or crawling insects. They exhibit repellent as well as knockdown and kill activity against insects. Pyrethroids are not harmful to plants, food, animals or humans, and leave no harmful residues. Therefore, they are allowed to be applied on clothes in all countries. Despite these highly favorable characteristics, pyrethroid has had only limited general utility on cloth because of its relatively short-lived insecticidal action. This is due to the poor washing fastness of common finishing formulas, and decomposition of pyrethroid into a nonactive, non-insecticidal product in the presence of oxygen and ultraviolet light.

To prior inventions, U.S. Pat. No. 5,198,287 to Samson, et al. discusses a tent fabric with a water repellent and flame retardant coating that includes the insecticide permethrin. U.S. Pat. No. 5,252,387 to Samson teaches that permethrin can be preserved in insect repellent fabrics by placing a barrier over the permethrin. However, a problem with the prior art is retaining permethrin in washable garments through successive wash cycles.

U.S. Pat. No. 5,089,298 to McNally teaches that permethrin can be retained in garments impregnated with permethrin and amylopectin, a water insoluble form of starch, through a substantially greater number of laundering cycles than garments treated only with permethrin.

Whitcomb, U.S. Pat. No. 4,130,450 describes an insecticide-impregnated, open, low-density web that provides an expanded surface that may be loaded with contact insecticides, including pyrethrum and synthetically prepared insecticides. Whitcomb prefers the use of micro-encapsulated pyrethrum to avoid pyrethrum instability when exposed to ultraviolet light and oxygen. Whitcomb mentions that the web may be hung to permit vaporization of the active ingredient to combat flies.

Ronning et al., U.S. Pat. No. 4,765,982 is an example of the use of micro-encapsulated active ingredients to achieve a sustained release insect control effect. Pyrethroids, either synthetic or "natural", are cited as useful. The Ronning et al. insecticidal device may be hung in the open to achieve a repellent effect in a restricted locate to drive insects from a nest or the like.

The present invention addressed the deficiencies in the prior art by utilizing polymeric nanocapsules as opposed to binders and barriers, such nanocapsules having pyrethroid compounds for effectively prolonging the durability of insecticides, even after solar exposure and repeated launderings.

DESCRIPTION

The present invention proposes the manufacture of a fabric intended to be washable, such fabric having insecticidal properties through the incorporation of nanocapsules with pryethroid compounds.

Through the methods of the present invention, the manufactured fabrics are capable of retaining the insecticide properties through successive washings and solar exposures.

These and other features, aspects, and advantages of the apparatus and methods of the present invention will become better understood from the following description, appended claims, and accompanying drawings where:

The following description of certain exemplary embodiment(s) is merely exemplary in nature and is in no way intended to limit the invention, its application, or uses. Throughout this description, the term "nanocapsule(s)" refers to particle(s) in nanosize that exhibits different physical properties than the bulk material or larger size from which it is derived.

Figure 1:
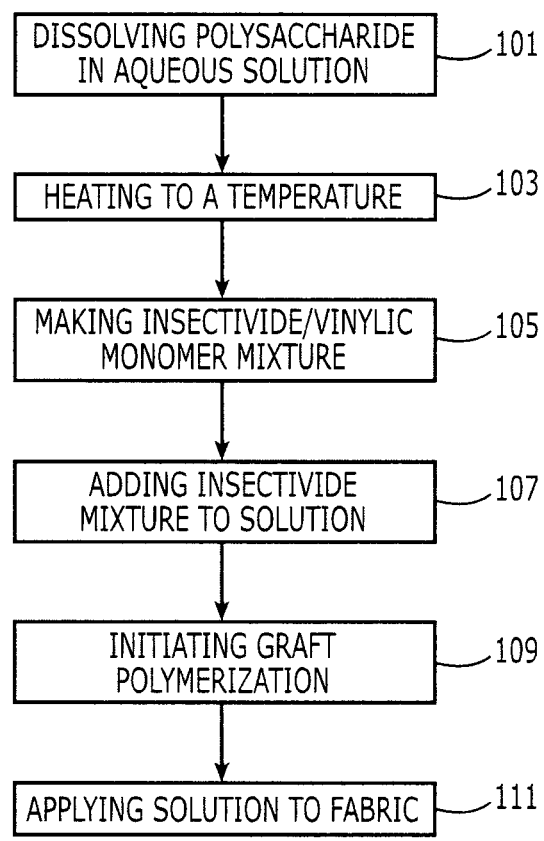
FIG. 1 shows a method of making insecticide-treated fabrics in accordance with the present invention.
Figure 2:
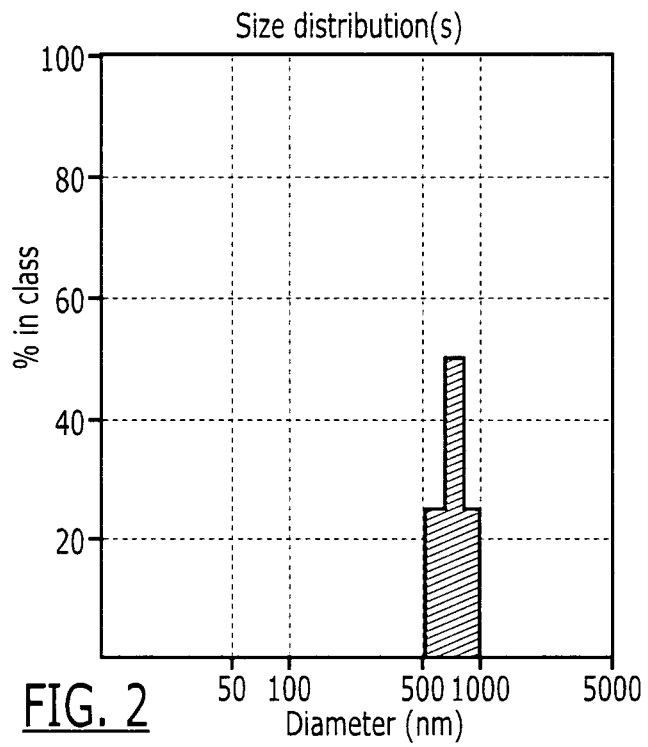
FIG. 2 shows the diameters of the nanocapsules utilized in the present invention.
Figure 3:
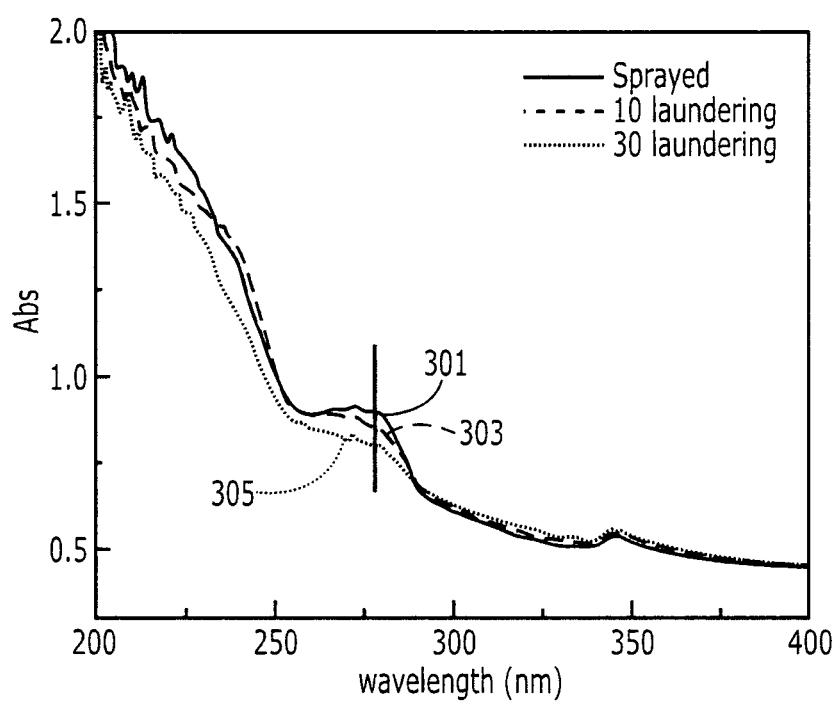
FIG. 3 shows a fabric retaining the insecticide properties after successive washings.

Now, to FIGS. 1-3,

The present invention relates to methods for making products of a fabric incorporating polymeric nanocapsules having a pyrethroid compound. The resultant products show improved efficiency as an insect repellant, even following successive washings and solar exposures.

FIG. 1 shows the method of making fabrics with polymeric nanocapsules having a pyrethroid compound, including the steps of dissolving a polysaccharide compound 101, heating the resultant solution 103, making an insecticide mixture 105, adding the mixture to the solution 107, initiating graft polymerization in the solution 109, and applying the solution to a fabric 111.

A polysaccharide compound is firstly dissolved in an aqueous solution 101, for example water (deionized, distilled, etc.) or water possessing a base, such as NaOH, or acid, such as acetic acid. The polysaccharide compound can be selected from the group consisting of amylopectin, arabian gum, carrageenan, cellulin, chitosan, chitin, cellulose such as methyl cellulose, carboxymethyl cellulose, and hydroxyehtyl cellulose, gellan gun, natural gum, pectin, polysaccharide peptide, starch, xanthan gum, and xyloglucan. The amount of polysaccharide that can be dissolved can be from about 0.5 g to about 5 g. Water can be in an amount of from about 70 mL to about 100 mL. When a base or acid is added to the water, it can be in an amount of from about 1 to 3 mL. In one embodiment, dissolving occurs under stirring. After dissolving, the solution is heated 103. Heating may occur between from about 60° C. to about 80° C. In one embodiment, heating is accomplished in a flask equipped with a condenser. Heating can be followed by purging with an inert gas, such as nitrogen ($N_2$). Heating can occur from approximately 15 minutes to 45 minutes.

An insecticide/vinylic monomer mixture is then made 105. The mixture contains a prytheroid compound as the insecticide, such compound being selected from the group consisting of pyrethrin, permethrin, cypermethrin, and phenothrin. Suitable vinylic monomers can be in the form of a vinyls, a diene, an acrylate monomer, or an acrylamide monomer. Examples of vinylic monomers include those of the formula $R^1R^2C{=}CH_2$, where $R^1$ hydrogen or alky, and where $R^2$ is alkyl, aryl, heteroaryl, halo cyano, or other suitable hydrophobic group. Groups for $R^1$ include hydrogen and methyl. Groups for $R^2$ include $C^1$-$C^6$ alkyl; phenyl; monocyclic heteroaryl with 4 to 8 ring atoms, more preferable 5 to 6 ring atoms, and with 1, 2 or 3 ring heteratoms, preferably 1 or 2, more preferably 1 ring atom, selected from nitrogen, oxygen or sulfur; chloro; and cyano. Examples of dienes include those of formula $CH_2{=}C(R^1){-}C(R^2){=}CH_2$ where $R^1$ is hydrogen or halogen or alkyl, and where $R^2$ is hydrogen or alkyl, such as $C_1$-$C_6$ alkyl. Groups for $R^1$ include hydrogen, chloride and methyl. Groups for $R^2$ include hydrogen and methyl. Examples of acrylate monomers include those of formula $CH_2=CR^3-COOR^4$, where $R^3$ is hydrogen or alky, and where $R^4$ is alkyl or substituted allyl, or other suitable hydrophobic group. Groups for $R^3$ include hydrogen and methyl. Groups for $R^4$ include $C_1$-$C_{16}$, for example $C_1$-$C_{12}$, alkyl which may be straight-chain or branched, and such groups substituted with one or more substituents chosen from unsubstituted amino, monosubstituted amino, disubstituted amino, hydroxyl, carboxy, or other usual acrylate substituent. Acrylate monomers can comprise methyl methacrylate, ethyl methacrylate, isopropyl methacrylate, n-butyl methacrylate, and the like. Examples of acrylamide monomers include those of formula $CH_2=CR^3-COONHR^4$, where $R^3$ and $R^4$ are as defined. Other suitable vinyl monomers include vinyl acetate, styrene, and maleic anhydride.

Possible types of vinyl monomers are shown in table 1.

TABLE 1

Structures of Various Vinyl Monomers

| Type of Vinyl Monomer | R | R' |
|---|---|---|
| Vinyls $CH_2=\overset{R}{\underset{R'}{C}}$ | —H<br>—$CH_3$<br>—Cl | Alkyl<br>Phenyl<br>Pyridine<br>—Cl<br>—CN<br>—OAc |
| Diene $CH_2=\overset{R}{\underset{}{C}}-\overset{R'}{\underset{}{C}}=CH_2$ | —H<br>—Cl<br>—$CH_3$ | H<br>$CH_3$ |
| Acrylates $CH_2=\overset{R}{\underset{\underset{OR'}{C=O}}{C}}$ | —H<br>—$CH_3$ | Linear or branched alkyl groups<br>Alkyl groups containing functional groups such as amine, hydroxyl, carboxylic acid etc. |
| Acrylamides $CH_2=\overset{R}{\underset{\underset{\underset{R'}{NH}}{C=O}}{C}}$ | —H<br>—$CH_3$ | Linear or branched alkyl groups<br>Alkyl groups containing functional groups such as amine, hydroxyl, carboxylic acid etc. |

The concentration of the mixture can be in the range of from about 0.1M to about 3M.

The mixture is added to the solution 107, along with an initiator. Suitable initiators for addition to the solution include those suitable for radical polymerization. As is well-known in the art, radical polymerization requires the generation of free radicals capable of reacting with the monomer. Suitable initiators include peroxides such as benzoyl peroxide, +–Butyl peroxide, +–Butyl hydroperoxide, sec-Butyl peroxydicarbonate, azobisisabutyronitrile, ammonium persulfate, potassium persulfate, 2,2'-azobis(2-methyl propion amidine) dihydrochloride (V-50), and cerium. In one embodiment, reducing agents may be added to the solution, for example melid ions in their reduced state. Examples of reducing agent include $Fe^{2+}$, $Co^+$, $Cr^{2+}$, and $V^2$. At the laboratory scale, the initiator may be added in an amount of from about 0.5 g to about 9 g. Scaling up of the mixture to an industrial level may require larger amount of initiator, which would be well known to one in the art.

Initializing polymerization in the solution can be brought by heating the solution 109. The solution can be heated from between 55° C. to about 85° C. for about from 5 hours to about 9 hours.

The method produces particles in the range of from about 100 nm to about 1000 nm. In a preferred embodiment, the particles are from 400 to 900 nm.

The particles in solution are then applied to the fabric 111, for example cottons, polyesters, cotton/polyester blends, wool, and nylon. The emulsion (particles in solution) may be applied using techniques known in the art, such as immersion, spraying, and dipping. In one embodiment, the emulsion is applied by immersing the fabric in the emulsion. The fabric may be exposed to the emulsion on one side, or both sides. Included with applying the emulsion, the treated fabric may be further padded, dried cured, and the like.

EXAMPLES

Example 1

Deionized water 97 mL was mixed with acetic acid 1 mL to dissolve chitosan 0.5 g. After being filtered to eliminate insoluble impurities, the solution was heated to 80° C., in a flask equipped with a condenser, and purged with $N_2$ under stirring for half an hour. After that, a mixture of 2 mL vinyl acetate and 1.0 g permethrin was added into the solution, following by addition of 2 mL 20 mM tert-butyl hydrogenperoxide (TBHP) solution. The reaction was kept at 70° C. for 6 hours.

The resultant particle size was between 500-700 nm. The emulsion was then applied to a cotton/polyester fabric.

Example 2

Deionized water 80 mL was mixed with NaOH 0.1 g to gelatinized 5 g amylopectin at 70° C. under stirring, in a flask equipped with a condenser. After gelatinizaion, 0.2 g maleic anhydride was added into the amylopectin solution, to neutralize the NaOH. The solution was purged with $N_2$ for half an hour. Then a mixture of 10 mL styrene and 5 g phenothrin was added into the solution, following by addition of 0.5 g ammonium persulfate. The reaction was kept at 70° C. for 8 hour. Therein the polymeric nanocapsule size range is 500-1000 nm. The emulsion was then applied to a cotton/polyester fabric via immersing.

Example 3

Deionized water 72 mL was used to dissolve 5 g hydroxyethyl cellulose. The solution was heated to 60° C. in a flask equipped with a condenser, and purged with $N_2$ under stirring for half an hour. Then a mixture of 10 mL ethyl acrylate and 5 g pyrethrin was added into the solution, following by addition of 8 g ammonium cerium nitrate. The reaction was kept at 60° C. for 8 hour. Therein the polymeric nanocapsule size range is 400-900 nm. The emulsion was then applied via immersing the fabric.

Example 4

Deionized water 87 mL was used to dissolve 5 g Arabian gum. The solution was heated to 70° C. in a flask equipped with a condenser, and purged with $N_2$ under stirring for half an hour. Then a mixture of 5 mL butyl acrylate and 3 g cypermethrin was added into the solution, following by addition of 0.3 g 2,2'-azobis (2-methylpropion amidine) dihydrochloride (V-50). The reaction was kept at 70° C. for 8 hour. Therein the polymeric nanocapsule size range is as narrow as 400-750 nm.

FIG. 2 shows the particle size range for particles made in accordance with the present method. As shown, the range generally extended from about 50 nm to about 1000 nm, with the largest number of particles at around 900 nm.

Example 5

Application of Emulsion to Fabric

The fabric substrate is a 65/35 cotton/polyester blend. The fabric is immersed in the emulsion or dispersion for 1 min, padded with a wet pick-up of 70 wt %. After padding, the fabric is dried in oven at 80° C. for 3 min, and cured at 160° C. for 3 min.

The following examples test the efficiency of fabric treated with the present invention:

Mosquito Repellency Test

The mosquito repellent test was carried out according to a modified Chinese standard GB/T 17322.10-1998. In brief, placing the test fabric sample (4×4 cm$^2$) over a person's hand back that is covered around by a rubber glove. Inserting the covered hand into a cage (40×30×30 cm$^2$) containing approximate 300 mosquitoes (*Aedes albopictus*). Commonly three testees are selected to perform the same exposure to mosquitoes. The average alighting number and the number of person stung during the time (2 min) that the textile is exposed to mosquitoes are recorded.

Dust-Mite Repellency Test

The dust-mite repellent test was carried out according to a Chinese standard GB/T 17322.1-12-1998. 7 glass dished (diameter 6.0 cm, height 1.5 cm) were employed, using 6 among them to surround the remain one. Contacts between each other were fixed by adhesive tapes. In the centered-dish, more than 1000 mites were added. In the surround-dishes, blank cloth and cloth sample were added one after one, together with 0.05 f food for mite. All these apparatus were set in a covered disk (30*20*5 cm), where saturate solution of NaCl was added to keep the air-humidity at 75%. The test was operated at a constant temperature of 25° C. Observe the quantity of mites on blank fabric and treated fabric separately within 24 h. For each sample, the test should repeat 3 times, and average was taken. The mite repellency was calculated as repellency (%)=(1−Number on sample/number on blank) *100.

Anti-Bacterial Test

According to the Corporate Test Method 0923 by Dow Corning (1979), *Ataphylococcus aureus* (ATCC 6538), a gram-positive type of bacteria, was employed to test the antibacterial activity of textiles treated with emulsions. 25 μL bacterial culture was diluted with 900 mL 0.5 mMPBS solution at pH5.00. Cotton textile sprayed with emulsion was cut into little pieces and put into 50 mL bacterial solution, under shaking of 150 rpm. The amount of bacteria in solution was evaluated by monitoring the optical absorbance of solution at 600 nm. The antibacterial activity of sample was evaluated by the reduction of bacteria in culture within 2 hours.

The AATCC Laundering Procedure

All of the AATCC launderings in the examples were done following the AATCC test method 61-2003 test no. 2A. An AATCC standard wash machine (Atlas Launder-Ometer) and detergent (AATCC Standard Detergent WOB) was used. Samples were cut into 5×15 cm swatches and put into a stainless steel container with 150 ml of 0.15 w/v % WOG detergent solution and 50 steel balls (0.25 in. in diameter) at 49° C. for various washing time to mimic 10, 20 and 30 wash cycle of home/commercial launderings. Insecticide retention after launderings was measure and compared.

The instrument and test procedure that were used for in-situ determining the quantity of insecticide remaining in the fabric after launderings is set forth below:

Instrument: a Varian Cary 300 UV-Spectrophotometer.

Test procedure: Prepare dilute solutions of permethrin in ethanol (1/1000-1/1000 g/ml); Place a test specimen into the light-path, and measure the characteristic absorption of permethrin in UV spectrum. The characteristic absorption peak of peremethrin was recognized at 235 nm, and there is a proportional relevant between permethrin content and peak intensity.

Calculation procedure: Compare the absorption intensities at 235 nm in UV spectra recorded for treated fabrics and washed fabrics, the remained percent of permethrin can be concluded.

Insecticide Retention after Solar Exposure

The solar exposure durability of insecticide encapsulated in polymeric nanocapsule was monitored by exposing the treated fabric to solar for a desired period, then to test its mosquito repellency again.

Example 6

A: The fabric is padded with a mixture of polyurethane binder (Ciba, DICRYLAN PMC, containing polyurethane 50 wt %) 5 g, 85 mL water, and 10 mL ethanol solution containing 1 g permethrin.

B: the fabric was padded with the formulation Example 1.

For the produced fabrics "A" and "B", their mosquito repellency and insecticide retention during launderings were compared. Polymer/insecticide=2.5/1; insecticide amount 0.84 g/m$^2$.

Mosquito Repellency

| Fabrics (4 * 4 cm$^2$) | Standing mosquito No. (in 2 min.) | Stung persons (Total 3) |
| --- | --- | --- |
| A | 28 | 2 |
| B | 12 | 1 |

Permethrin Retention

| | 10 Launderings/ | 20 Launderings |
| --- | --- | --- |
| A | 62% | 35% |
| B | 80% | 65% |

The polymeric nanocapsule provides better mosquito repellency and higher insecticide retention during washing than the polymeric binder. This result mainly is due to the larger surface area, finely encapsulation and hydrophobicity of vinyl polymer in the case of polymeric nanocapsule.

Example 7

Comparison of Insecticide Relation During Washing and Mosquito Repellency from Different Emulsions In this example, the fabric substrate is a 50/50 cotton/nylon fabric for battle dress uniforms. The fabric is immersed in the emulsion for 1 min, padded with a wet pick-up of 70 wt %. After padding, the fabric is dried in oven at 80° C. for 3 min, and cured at 160° C. for 3 min.

A: The fabric is padded with the emulsion from Example 1.

B: The fabric is padded with a mixture of the emulsion from Example 2 20 g and 80 mL water.

C: The fabric is padded with a mixture of them emulsion of the emulsion from Example 3 20 g, 80 g water, and 1.0 g polyurethane binder (Ciba, DICRYLAN PMC, containing polyurethane 50 wt %)

D: The fabric is padded with a mixture of the emulsion Example 4 30 g, 60 g water, and 2.0 g polyurethand binder (Ciba, DICRYLAN PMC, containing polyurethane 50 wt %)

For the produced fabrics A, B, C, and D, their mosquito repellency and insecticide retention during launderings were compared. Polymer/insecticide=2.5/1; insecticide amount 0.84 g/m$^2$.

Mosquito Repellency

| Fabrics (4 * 4 cm2) | Standing mosquito No. (in 2 min.) | Stung persons (Total 3) |
|---|---|---|
| A | 12 | 1 |
| B | 11 | 1 |
| C | 19 | 1 |
| D | 17 | 1 |

Permethrin Retention

|  | 10 Launderings | 20 Launderings |
|---|---|---|
| A | 80% | 65% |
| B | 82% | 60% |
| C | 10% | 49% |
| D | 68% | 43% |

The emulsion Example 1 and Example 2 provide better mosquito repellency and higher insecticide retention during washing than the mixtures of Example 3 and Example 4 with the polyurethane binder. This difference may be due to the insolubility of the dried polymeric nanocapsules from "E1" and "E2" at laundering conditions, meanwhile the dried polymeric nanocapsules from "E3" and "E4" may dissolve into the laundering solution although their links to fabric was improved by the polymeric binder.

Example 8

Comparison of insecticide retention during washing and mosquito repellency by different drying conditions after padding.

In this example, the fabric substrate is a 100% cotton Rip-Stop fabric intended for a military battle dress uniform. The fabric is immersed in the emulsion Example 1 for 1 min, padded with a wet pick-up of 70 wt %. Then it is dried at different temperatures. Polymer/insecticide=2.5/1; insecticide amount 0.84 g/m$^2$.

A: the fabric is oven-dried at 80° C. for 5 min.

B: the fabric is air-dried at room temperature.

For the produced fabrics A and B, their mosquito repellency and insecticide retention during launderings were compared. Polymer/insecticide=2.5/1; insecticide amount 0.84 g/m$^2$.

Mosquito Repellency

| Fabrics (4 * 4 cm2) | Standing mosquito No. (in 2 min.) | Stung persons (Total 3) |
|---|---|---|
| A | 11 | 1 |
| B | 8 | 0 |

Permethrin Retention

|  | 10 Launderings | 20 Launderings |
|---|---|---|
| A | 80% | 57% |
| B | 90% | 71% |

The air-drying at room temperature rather than the oven-drying at high temperature provides better mosquito repellency and higher insecticide retention during washing. Seemly the drying at a temperature higher than the melting point of insecticide (e.g., permethrin melts at about 40° C.) may change the distribution of the insecticide in the dried polymeric film, and thus effect its washing durability and mosquito repellency.

FIG. 3 shows the absorbance levels of the fabric following multiple launderings.

Example 9

Comparison of Mosquito Repellency, Mite Repellency, Antibacterial Activity from Spraying and Padding In this example, the fabric substrate is a 100% cotton plain weave fabric. The fabric is finished with the emulsion Example 1 in different processes.

A: the fabric is immersed in the emulation Example 1 for 1 min, padded with a wet pick-up of 60 wt %. Then it is air-dried at room temperature.

B: the fabric is sprayed with a wet pick-up of 60% on only one side, and air-dried at room temperature. During repellency test, this sprayed fabric is exposed with the sprayed side to the insects. Polymer/insecticide=2.5/1; insecticide amount 0.72 g/m$^2$.

Insert Repellency

| Fabrics (4 * 4 cm2) | Standing mosquito No. (in 2 min.) | Stung persons (Total 3) | Mite repellency (%) | Bacteria reduction (%) |
|---|---|---|---|---|
| A | 10 | 0 | 85 | 93 |
| B | 7 | 0 | 92 | 95 |

It is apparent from this data that fabrics that are surface sprayed with emulsion have a greater insect repellent efficacy than fabrics that are padded with equal amounts of emulsion. It is reasonable to consider that when spray, most of the reagent is located on one major surface of the fabric, although there may be a little diffusion and penetration into fibers inside and another surface of the fabric. In padding, the same quantity of emulsion is dispersed throughout the body of the fabric. Consequently, only the portion of the reagent that is located on the surface of the fabric that becomes the outer surface of a garment is available for the repellency of insects. The rest of the reagent is scattered throughout the fabric, with as much of the reagent on the inside of a garment made from the fabric as there is on the outside. Therefore, the surface spraying creates a more efficacious insect control fabric. Another advantage of surface spraying fabric intended for garments is that a surface spraying on the outside of the garment minimizes skin contact to the wearer and maximizes the location of permethrin for contact by insects. In addition, because of the presence of chitosan, this formula also provides perfect anti-bacterial function to the finished clothes.

Example 10

Solar Exposure Durability of Mosquito Repellency from Polymeric Manocapsule Containing Insecticide In this example, the fabric substrate is a 100% cotton plain weave fabric. The fabric is sprayed by emulsion Example 1 with a wet pick-up 50 wt % on only one side, and air-dried at room temperature. Thus treated fabrics were exposed to solar light for desired periods via hanging out-doors, and thereafter were measured on the mosquito repellency to check its solar durability. Polymer/insecticide=2.5/1;, insecticide amount 0.60 g/m$^2$.
A: the fabric is hanged out-doors under sun-shine for 1 month.
B: the fabric is hanged out-doors under sun-shine for 3 months.
For the produced fabrics A and B, their mosquito repellency was compared. Polymer/insecticide=2.5/1; insecticide amount 0.84 g/m$^2$.
Mosquito Repellency

| Fabrics (4 * 4 cm2) | Standing mosquito No. (in 2 min.) | Stung persons (Total 3) |
|---|---|---|
| A | 9 | 0 |
| B | 13 | 0 |

The fabric finished with the polymeric nanocapsule containing insecticide was solar durable, and can provide good mosquito repellency even exposed to solar light for 3 months.

Example 11

Mosquito Repellency and Other Practical Function from Emulsion Comprising Polymeric Nanocapsule and Softener, and Fragrant or Synergist In this example, the fabric substrate is a 100% cotton plain weave fabric. The fabric is sprayed by a mixture of emulsion Example 2 and other functional components, with a wet pick-up of 50 wt % on only one side, and air-dried at room temperature. Thus treated fabrics were measured on the mosquito repellency and other desired properties.
A: the fabric is sprayed by a mixture of emulsion Example 2 20 g and 80 mL water.
B: the fabric is sprayed by a mixture of emulsion Example 2 20 g, 70 mL water, and 10 g softener.
C: the fabric is sprayed by a mixture of emulsion Example 2 20 g, 79 mL water, and 1 mL citral.
D: the fabric is sprayed by a mixture of emulsion Example 2 20 g, 78 mL water, and 2 mL octachorodipropylether.
For the produced fabrics A, B, C, and D, their mosquito repellency and other practical functions were compared. Polymer/insecticide=2.5/1; insecticide amount 0.60 g/m$^2$.
Mosquito Repellency

| Fabrics (4 * 4 cm2) | Standing mosquito No. (in 2 min.) | Stung persons (Total 3) |
|---|---|---|
| A | 7 | 0 |
| B | 9 | 0 |
| C | 5 | 0 |
| D | 3 | 0 |

Other Practical Function

Among these specimens, the B provides an additional super-soft hand feel, the C provides an additional fragrant smell, and the D provides the most strong mosquito repellency.

The emulsion of polymeric nanocapsule containing insecticide can be used together with many other functional reagents to give out comprehensive practical performances and satisfying mosquito repellency.

Having described embodiments of the present system with reference to the accompanying drawings, it is to be understood that the present system is not limited to the precise embodiments, and that various changes and modifications may be effected therein by one having ordinary skill in the art without departing from the scope or spirit as defined in the appended claims.

In interpreting the appended claims, it should be understood that:

a) the word "comprising" does not exclude the presence of other elements or acts than those listed in the given claim;

b) the word "a" or "an" preceding an element does not exclude the presence of a plurality of such elements;

c) any reference signs in the claims do not limit their scope;

d) any of the disclosed devices or portions thereof may be combined together or separated into further portions unless specifically stated otherwise; and e) no specific sequence of acts or steps is intended to be required unless specifically indicated.

The invention claimed is:

1. A method of making a pyrethroid compound-treated fabric comprising cellulosic fiber, cotton, polyesters, cotton/polyester blends, wool, nylon, or a combination thereof; and
   polysaccharide-based polymeric nanocapsules having a pyrethroid compound encapsulated therein, the polysaccharide-based nanocapsules being deposited on the fabric,
   wherein the nanocapsules are sized between 100 nm to 1000 nm and are graft polymers of a hydrophobic vinyl monomer and a hydrophilic polysaccharide,
   wherein the hydrophilic polysaccharide contains at least one hydroxyl group forming a hydrogen bond with the fabric,
   the method comprising
   (a) dissolving a polysaccharide compound in an aqueous solution;
   (b) heating the solution of dissolved polysaccharide of (a);
   (c) adding a pyrethroid mixture to the heated solution of (b);
   (d) initiating graft polymerization in the pyrethroid mixture-containing solution of (c); and (e) applying the solution of (d) having undergone graft polymerization to the fabric.

2. The method of making a pyrethroid compound-treated fabric of claim 1, wherein the polysaccharide compound is selected from the group consisting of amylopectin, arabian gum, carrageenan, cellulin, chitosan chitin, methyl cellulose, carboxymethyl cellulose, hydroxyethyl cellulose, gellan gum, natural gum, pectin, polysaccharide peptide, starch, xanthan gum, and xyloglucan.

3. The method of making a pyrethroid compound-treated fabric of claim 1, wherein the aqueous solution is selected from the group consisting of distilled water, deionized water, aqueous NaOH, and aqueous acetic acid.

4. The method of making a pyrethroid compound-treated fabric of claim 2, wherein from 0.5 g to 5 g of the polysaccharide is dissolved.

5. The method of making a pyrethroid compound-treated fabric of claim 1, wherein the heating occurs between about 60° C. to 80° C. for approximately 15 minutes to 45 minutes.

6. The method of making a pyrethroid compound-treated fabric of claim 1, further comprising purging the solution with $N_2$ after heating the solution.

7. The method of making a pyrethroid compound-treated fabric of claim 1, wherein the pyrethroid mixture comprises a pyrethroid compound selected from the group consisting of pyrethrin, permethrin, cypermethrin, and phenothrin, and a hydrophobic vinylic monomer.

8. The method of making a pyrethroid compound-treated fabric of claim 7, wherein the hydrophobic vinylic monomer is selected from the group consisting of a vinyl monomer of Formula (I), (II), (III), and (IV):

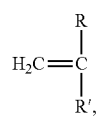
(I)

wherein R is H, $CH_3$, or Cl, and $R^1$ is alkyl, phenyl, pyridine, Cl, CN, or OAc;

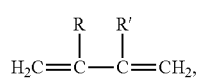
(II)

wherein R is H, Cl, or $CH_3$, and $R^1$ is H or $CH_3$;

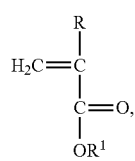
(III)

wherein R is H or $CH_3$, and $R^1$ is a linear or branched alkyl group or an alkyl group having an amine, hydroxyl, or carboxylic acid group; and

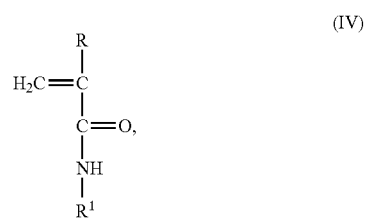
(IV)

wherein R is H or $CH_3$, and $R^1$ is a linear or branched alkyl group or an alkyl group having an amine, hydroxyl, or carboxylic acid group.

9. The method of making a pyrethroid compound-treated fabric of claim 7, wherein the pyrethroid in the mixture has a concentration of from 0.1M to 3M.

10. The method of making a pyrethroid compound-treated fabric of claim 1, further comprising adding an initiator to the solution of (c) after adding the pyrethroid mixture.

11. The method of making a pyrethroid compound-treated fabric of claim 10, wherein the initiator is selected from the group consisting of benzoyl peroxide, +/−butyl peroxide, +/−butyl hydroperoxide, sec-butyl peroxydicarbonate, azobisisabutyronitrile, ammonium persulfate, potassium persulfate, 2,2'-azobis(2-methyl propion amidine)dihydrochloride (V-50), and cerium.

12. The method of making a pyrethroid compound-treated fabric of claim 1, wherein initiating graft polymerization occurs by heating the solution from between 55° C. to 85° C. for 5 to 9 hours.

13. The method of making a pyrethroid compound-treated fabric of claim 1, wherein (e) occurs by immersing at least one side of the fabric in the solution.

14. The method of making a pyrethroid compound-treated fabric of claim 13, wherein the fabric is selected from the group consisting of cottons, polyesters, cotton/polyester blends, wool, and nylons.

15. A pyrethroid compound-treated fabric comprising
cellulosic fiber, cotton, polyesters, cotton/polyester blends, wool, nylon, or a combination thereof; and
polysaccharide-based polymeric nanocapsules having a pyrethroid compound encapsulated therein, the polysaccharide-based nanocapsules being deposited on the fabric,
wherein the nanocapsules are sized between 100 nm to 1000 nm and are graft polymers of a hydrophobic vinyl monomer and a hydrophilic polysaccharide,
wherein the hydrophilic polysaccharide contains at least one hydroxyl group forming a hydrogen bond with the fabric.

16. The pyrethroid compound-treated fabric of claim 15, wherein the vinyl monomer is selected from the group consisting of a vinyl monomer of Formula (I), (II), (III), and (IV):

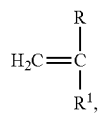
(I)

wherein R is H, CH$_3$, or Cl, and R$^1$ is alkyl, phenyl, pyridine, Cl, CN, or OAc;

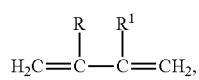
(II)

wherein R is H, Cl, or CH$_3$, and R$^1$ is H or CH$_3$;

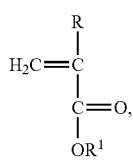
(III)

wherein R is H or CH$_3$, and R$^1$ is a linear or branched alkyl group or an alkyl group having an amine, hydroxyl, or carboxylic acid group; and

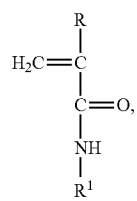
(IV)

wherein R is H or CH$_3$, and R$^1$ is a linear or branched alkyl group or an alkyl group having an amine, hydroxyl, or carboxylic acid group.

17. The pyrethroid compound-treated fabric of claim 15, wherein the pyrethroid compound is selected from the group consisting of pyrethrin, permethrin, cypermethrin, and phenothrin.

18. The pyrethroid compound-treated fabric of claim 15, wherein the nanocapsules are sized from 400 nm to 900 nm.

19. The pyrethroid compound-treated fabric of claim 15, wherein the pyrethroid compound-treated fabric is capable of retaining insecticide properties through successive launderings and solar exposures.

20. The pyrethroid compound-treated fabric of claim 15, wherein the hydrophilic polysaccharide containing at least one hydroxyl group is selected from the group consisting of amylopectin, arabian gum, carrageenan, cellulin, chitosan, chitin, methyl cellulose, carboxymethyl cellulose, hydroxyethyl cellulose, gellan gum, natural gum, pectin, polysaccharide peptide, starch, xanthan gum, and xyloglucan.

21. The pyrethroid compound-treated fabric of claim 15, wherein the nanocapsules are, or an emulsion containing the nanocapsules is, deposited on at least one side of the fabric.

\* \* \* \* \*